(12) United States Patent
Crainich

(10) Patent No.: US 8,758,392 B2
(45) Date of Patent: *Jun. 24, 2014

(54) CLOSING ASSEMBLIES FOR CLAMPING DEVICE

(75) Inventor: Lawrence Crainich, Charlestown, NH (US)

(73) Assignee: Design Standards Corporation, Charlestown, NH (US)

( * ) Notice: Subject to any disclaimer, the term of this patent is extended or adjusted under 35 U.S.C. 154(b) by 422 days.

This patent is subject to a terminal disclaimer.

(21) Appl. No.: 12/622,700

(22) Filed: Nov. 20, 2009

(65) Prior Publication Data

US 2010/0069935 A1  Mar. 18, 2010

Related U.S. Application Data

(63) Continuation of application No. 10/995,782, filed on Nov. 22, 2004, now Pat. No. 7,641,671.

(51) Int. Cl.
*A61B 17/00* (2006.01)
*A61B 17/08* (2006.01)

(52) U.S. Cl.
USPC .......... 606/205; 606/151; 606/157; 606/158; 606/207

(58) Field of Classification Search
USPC ......... 606/120, 151, 157, 158, 205, 207, 142; 227/176.1
See application file for complete search history.

(56) References Cited

U.S. PATENT DOCUMENTS

| 4,173,903 | A | 11/1979 | Papke et al. |
| 4,640,117 | A | 2/1987 | Anderson et al. |
| 4,854,626 | A | 8/1989 | Duke |
| 4,880,015 | A | 11/1989 | Nierman |
| RE33,714 | E * | 10/1991 | Anderson et al. ............. 72/410 |
| 5,275,608 | A | 1/1994 | Forman et al. |
| 5,507,773 | A * | 4/1996 | Huitema et al. ............. 606/207 |
| 5,562,700 | A | 10/1996 | Huitema et al. |
| 5,562,701 | A | 10/1996 | Huitema et al. |
| 5,562,702 | A | 10/1996 | Huitema et al. |
| 5,626,607 | A | 5/1997 | Malecki et al. |
| 5,921,996 | A | 7/1999 | Sherman |
| 6,206,903 | B1 | 3/2001 | Ramans |
| 6,554,844 | B2 | 4/2003 | Lee et al. |
| 6,582,451 | B1 | 6/2003 | Marucci et al. |
| 7,097,650 | B2 | 8/2006 | Weller et al. |
| 2005/0049618 | A1 | 3/2005 | Masuda et al. |
| 2005/0177176 | A1* | 8/2005 | Gerbi et al. ................. 606/139 |

* cited by examiner

*Primary Examiner* — Julian W Woo

(74) *Attorney, Agent, or Firm* — Bachman & LaPointe, P.C.

(57) ABSTRACT

A closing assembly for a clamping device having first and second jaw members includes a closing mechanism connected between the first and second jaw members, the jaws extending distally from the closing mechanism; and a member for applying a separating force to the first and second jaw members proximally of the closing mechanism, whereby the first and second jaw members can be maintained substantially parallel during closing. The clamp has a very strong clamping force.

15 Claims, 4 Drawing Sheets

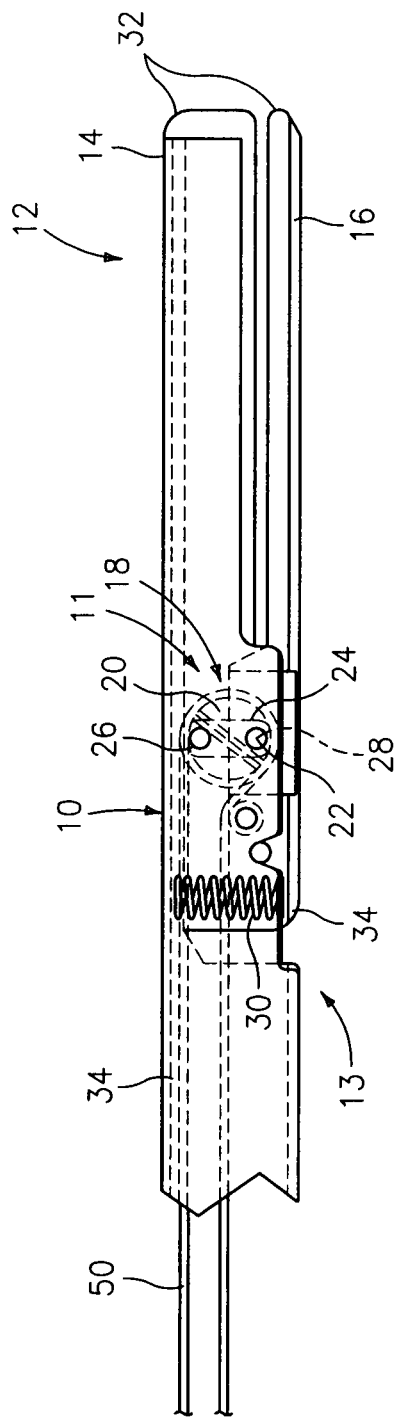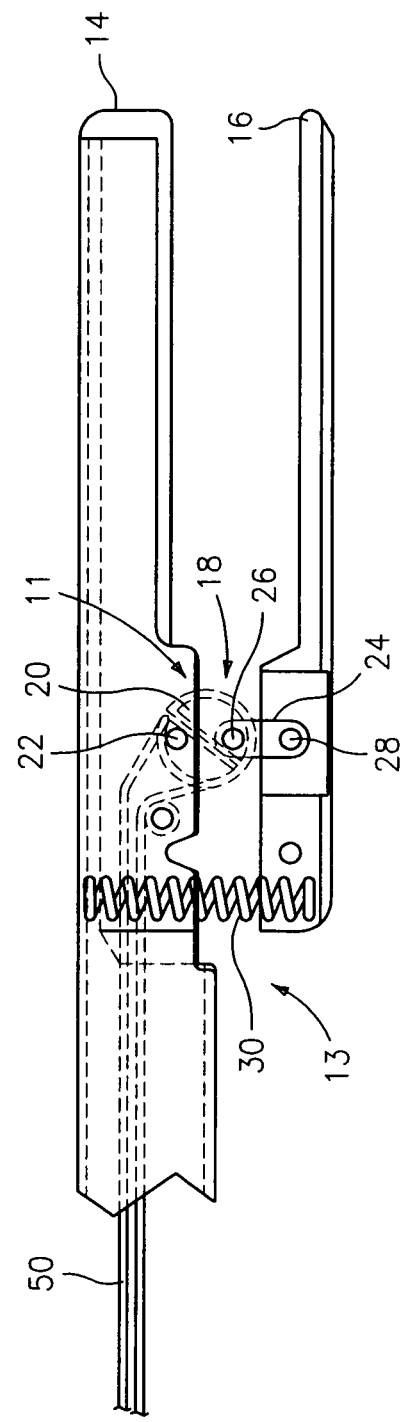

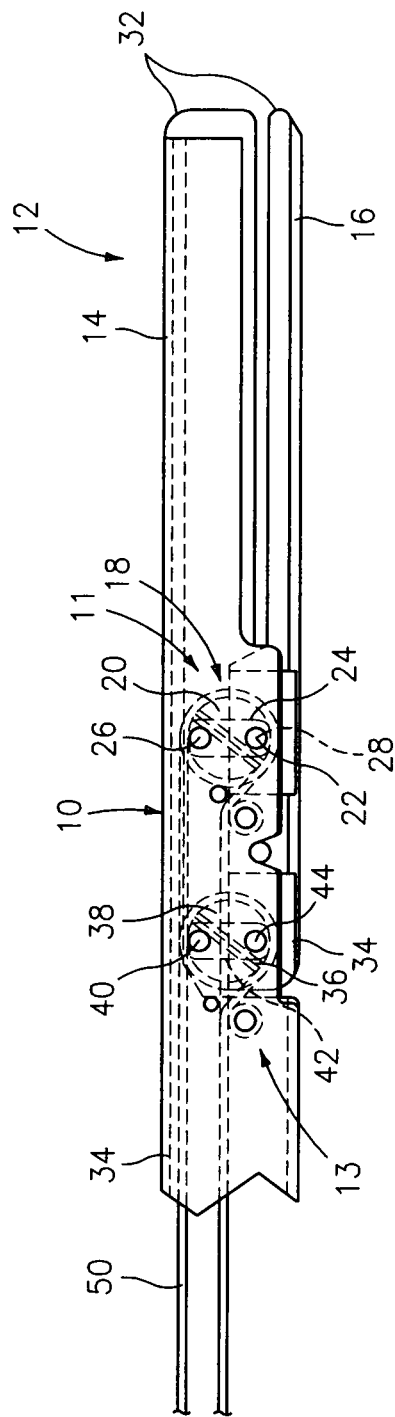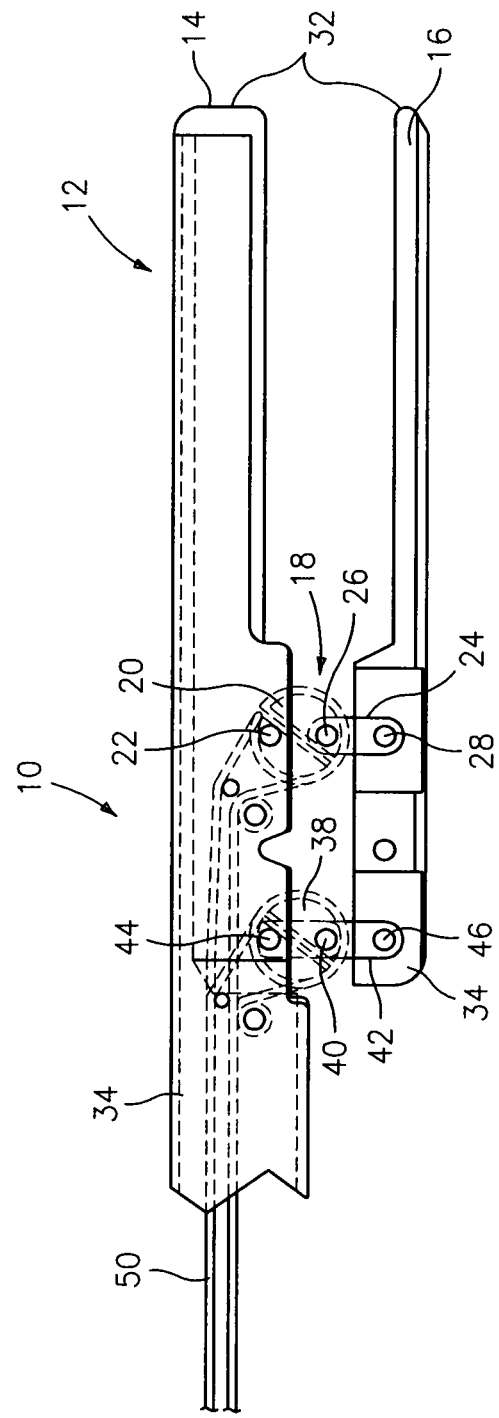
FIG. 3
FIG. 4

CLOSING ASSEMBLIES FOR CLAMPING DEVICE

CROSS REFERENCE TO RELATED APPLICATIONS

This application is the U.S. Continuation Application of U.S. application Ser. No. 10/995,782 filed Nov. 22, 2004, now U.S. Pat. No. 7,641,671.

BACKGROUND OF THE INVENTION

The invention relates to surgical instruments and, more particularly, to a closing assembly for a clamping device.

Various clamping devices are used during surgical and other medical procedures to grasp tissue and hold same as may be desired. The closing assemblies for such clamping devices typically involve a hinge and some mechanism for closing the jaws of the clamp mechanism around the hinge. Unfortunately, this can lead to "alligator" closing of the clamps, which can allow the tissue to be clamped to slip out of the jaws before the tissue is fully secured.

This issue with closing of conventional clamping mechanisms can lead to various problems and complications during procedures, since escape of tissue from the clamp can result in delays in surgical procedures, injury to the patient, and various other undesirable results.

Known clamping devices can also fail due to insufficient clamping force.

It is clear that the need remains for an improved closing assembly for such clamping devices.

It is therefore the primary object of the present invention to provide a closing assembly for a clamping device wherein "alligator" closing is avoided and a very strong clamping force is provided.

It is a further object of the present invention to provide a closing assembly for a clamping device which can be controlled to allow for a wide range of controlled motion of closing and opening of the jaw members from each other.

Other objects and advantages of the present invention will appear herein below.

SUMMARY OF THE INVENTION

In accordance with the present invention, the foregoing objects and advantages have been readily attained.

According to the invention, a closing assembly is provided for a clamping device having first and second jaw members, wherein the closing assembly comprises a closing mechanism connected between the first and second jaw members, the jaws extending distally from the closing mechanism; and means for applying a separating force to the first and second jaw members proximally of the closing mechanism, whereby the first and second jaw members can be maintained substantially parallel during closing.

In further accordance with the invention, the closing mechanism advantageously includes rotatable members, specifically rotatable disks, which are mounted relative to the jaws, and which have link members also rotatably mounted between the disks and the jaws, such that rotation of the disk causes the jaws to open and close. The means for applying a separating force can advantageously be a spring of various well-known design, or a second rotatable member or disk assembly, similar to the closing mechanism, either one of which can advantageously be used to prevent alligator closing of the jaws, by maintaining the jaws substantially parallel during closing.

The spring assembly serves to prevent alligator closing by applying a separating force to the proximal ends of the jaw members, which serves to keep these ends separated, and thereby to keep the distal ends of the jaws more closely aligned while the closing mechanism pulls them closed.

The assembly of the present invention provides for a very strong clamping force which is particularly desirable.

In the embodiment wherein the means for applying a separating force is a further rotatable member closing mechanism, these mechanisms can be operated or controlled together or independently, if desired, to provide for any desired orientation of jaws of the clamping device relative to each other.

In accordance with a further embodiment of the invention, wherein the means for applying a separating force is also a rotatable disk closing mechanism, the two closing mechanisms can be joined by a link such that driving of one closing mechanism operates both mechanisms.

BRIEF DESCRIPTION OF THE DRAWINGS

A detailed description of preferred embodiments of the present invention follows, with reference to the attached drawings, wherein:

FIG. 1 illustrates a closing assembly in accordance with the present invention;

FIG. 2 illustrates the closing assembly of FIG. 1 in a jaw-open position;

FIG. 3 illustrates a closing assembly in accordance with an alternative embodiment of the present invention;

FIG. 4 illustrates the closing assembly of FIG. 3 with the jaws in an open position;

DETAILED DESCRIPTION

Figure 5:
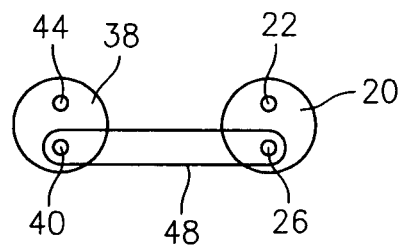
FIG. 5 illustrates a further alternative embodiment of the present invention.

The invention relates to a closing assembly for clamping devices, especially for clamping devices for surgical instruments. The closing assembly provides for an excellent clamping force and, also, for closing of the jaws with a desired orientation of the jaws relative to each other.

FIG. 1 shows a closing assembly 10 for a clamping device 12 wherein the clamping device has a first jaw 14 and a second jaw 16 which are used to grasp tissue and other items during surgical stapling or other procedures. Closing assembly 10 is advantageously used in accordance with the present invention to open and close jaws 14, 16, and particularly to close jaws 14, 16 with the jaws maintained in a desired orientation, preferably substantially parallel, during the closing movement.

FIG. 2 shows closing assembly 10 for clamping device 12 with jaws 14, 16 in an open position. The following descriptions should be considered with reference to both FIGS. 1 and 2.

According to the invention, closing assembly 10 advantageously includes a rotatable member 18 which is positioned relative to jaws 14, 16 such that rotation of rotatable member 18 causes opening and closing movement of jaws 14, 16 relative to each other.

In accordance with a preferred embodiment of the present invention, rotatable member 18 is provided in the form of one or more disks 20 which are rotatably mounted to jaw 14 at one point of rotation 22, and a link member 24 which is rotatably connected to disk 20 at a second point of rotation 26. Link 24 is also pivotably connected to jaw 16 at a point of rotation 28. Closing assembly 10 as illustrated in FIGS. 1 and 2 functions through rotation of disk 20 which pivots link 24 and causes or allows jaws 14, 16 to open to the position of FIG. 2 when rotated in one direction, and closes jaws 14, 16 to the position of FIG. 1 when rotated in the other direction.

The disk and link configuration of closing assembly 10 of the present invention advantageously allows for a very strong clamping force to be generated, which is particularly useful in surgical and other applications.

In accordance with the present invention, in addition to the closing mechanism portion of closing assembly 10, which is referred to in the drawings as closing mechanism 11, a member is provided for applying a separating force to jaw members 14, 16, which advantageously serves to prevent the above-described issues in connection with "alligator" closing of jaws 14, 16. In the embodiment shown in FIGS. 1 and 2, this member for applying a separating force is generally referred to as element 13, and in this embodiment is provided as a spring 30 compressed between proximal ends of jaws 14, 16 and applying a separating force to resist alligator closing of jaws 14, 16.

In connection with the present invention, jaws 14, 16 have distal ends 32 and proximal ends 34. In the embodiment shown, jaw 14 extends proximally further than jaw 16, and the portion referred to as proximal end 34 of this jaw 14 is actually not the end of the jaw. Nevertheless, at this portion, which is proximally located relative to closing mechanism 11, application of a separating force between ends 34 of jaws 14, 16 advantageously provides a force counter to the force applied by tissue being clamped between jaws 14, 16 such that jaws 14, 16 can be maintained substantially parallel during closing using closing mechanism 11.

In accordance with this embodiment of the present invention, the member 13 for applying a separating force is provided as a simple compressible spring. As an alternative, member 13 could be provided as leaf spring likewise positioned to exert a separating force against proximal ends 34 of jaws 14, 16 as desired.

It should readily be appreciated that this mechanism, in accordance with the present invention, advantageously serves to maintain jaws 14, 16 in a desired attitude, preferably substantially parallel relative to each other, during a clamping of tissue between jaws 14, 16. This serves to avoid orientation of jaws 14, 16 which would allow for tissue to escape during the clamping operation.

FIGS. 3 and 4 illustrate an alternative embodiment of the present invention. In this embodiment, closing mechanism 11 is the same as is described in connection with FIGS. 1 and 2, as are jaw members 14, 16. Thus, in connection with these elements, like reference numerals illustrate like parts. In accordance with this embodiment, however, the member 13 for applying a separating force is provided as a further rotatable member, or proximal rotatable member 36, which is similar in structure and operation to rotatable member 18 of closing mechanism 11. As shown, in this embodiment, rotatable member 36 is likewise provided as a disk 38 which is rotatably connected to jaw 14 at a pivot point 44, and a link member 42 is provided and rotatably connected to disk 38 at point 40 of rotation. Link 42 is also connected to jaw 16 at a second point 46 of rotation. With this configuration, and similar to operation of closing mechanism 11, when disk 38 is rotated, link 42 travels around the periphery of disk 38 and serves to open and close jaws 14, 16 depending upon direction of rotation of disk 38. It should be noted that the pivot point distances on the disk, that is, the distance between the pivot points on the disk, is preferably not identical to the distance between pivot points of the link. These distances can be selected to allow for various opening and closing options to be designed into the assembly. Thus, in accordance with this embodiment of the invention, the pivot point distance on the disk is different from the pivot point distance on the link. If these distances are the same, some other adaption may be needed to prevent mutual rotation of the link with the disk.

In the embodiment of FIGS. 3 and 4, member 13 for applying the separating force is actually a controllable member, and in this configuration jaws 14, 16 can be opened and/or closed with any desired orientation of one relative to the other. Thus, if it is desired to close jaws 14, 16 at a decreasing spacing, that is, the inverse of alligator closing, this can readily be accomplished through independent control or driving of member 13 relative to closing mechanism 11. Thus, the embodiment of FIGS. 3-4 allows for positioning of the jaws parallel or toed in or out as desired during the closing procedure.

FIG. 5 schematically shows a portion of a closing assembly 10 in accordance with a further preferred embodiment, wherein disks 20, 38 are utilized as the closing mechanism and means for applying a separating force respectively. In this embodiment, disks 20, 38 are linked using a link member 48 which is pivotably connected at pivot points of disks 20, 38 such that rotation of these disks is carried out simultaneously. Furthermore, in this embodiment, only one disk 20, 38 needs to be driven, and rotation of the driven disk will rotate the other disk as well. This serves to ensure that jaws 14, 16 are maintained substantially parallel during a closing procedure, of course, both disks can be driven if desired.

In the above-described Figures, disks 20, 38 have been described as having various different pivot points 22, 26, 40 and 44. At least one pivot point on the disk should be non-centric, that is, spaced from the center of the disk. This serves to generate the desired opening and closing motions when the disks are rotated. The distance of pivot points 22, 26 from the center of the disk helps to determine the rate and extent of opening and closing provided. Further structure of the disks is describe and shown below in connection with FIGS. 8 and 9.

Also in these embodiments, a drive member is provided for rotating the disks as desired. In the Figures, this drive member is provided as one or more cables 50 which are positioned around disks 20, 38 such that longitudinal movement of cables 50 generates pulley-like rotation of disks 20, 38 as desired. Cables 50 are particularly advantageous because they can be positioned to extend through the shaft of an elongate surgical instrument, for example such as that which is used in laparoscopic procedures. Cable 50 is further readily adapted to connection to various different trigger assemblies wherein longitudinal movement is utilized to control surgical instruments. Thus, cables 50 for use in driving disks 20, 38 should be readily adaptable to handle-members of various different surgical instruments.

Figure 6:
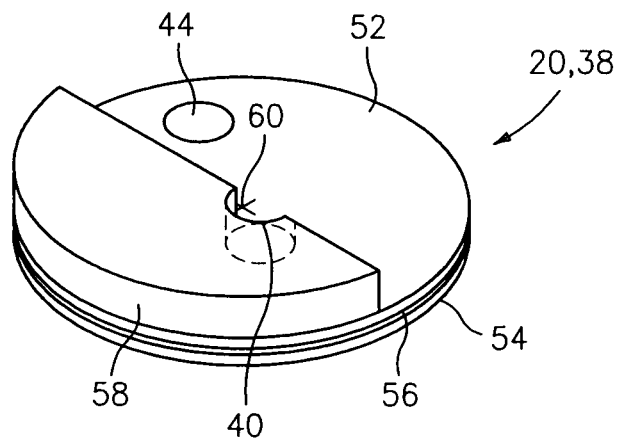
FIG. 6 is an enlarged view of a rotatable disk element of a closing assembly in accordance with the present invention.

Turning now to FIG. 6, a disk 20, 38 in accordance with the present invention is further illustrated. As shown, disk 20, 38 advantageously has two disk side portions 52, 54 which are separated by a peripheral groove 56 in which cable 50 can be positioned for pulley-like movement of disk 20, 38 as desired. In addition, one side 52 of disk 20, 38 is further advantageously provided with a thicker portion 58, which advantageously serves as a stop for a link pivotably connected to pivot point 26, 44. FIG. 6 further shows a center point 60 of disk 20, 38, and thereby illustrates the offset nature of pivot points 40, 44 relative to same.

Figure 7:
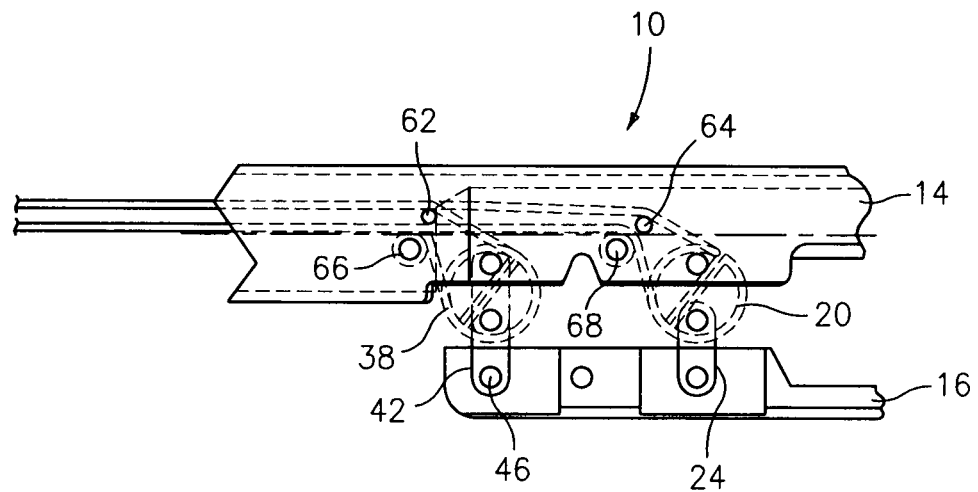
FIG. 7 better illustrates the drive mechanism of a closing assembly in accordance with the present invention.

Turning now to FIG. 7, the drive mechanism including cable 50 is better illustrated, with cable 50 shown in solid lines. As shown, cable 50 advantageously extends through jaw 14 and past a guide member 62 to then pass around disk 20. When cable 50 comes off of disk 20, it passes around a further guide member 64, and extends back out of jaw 14. Cables 50 can likewise extend past guide members 66, 68 to pass around disk 38, as well. In this manner, movement of cable 50 in pulley-like fashion serves to rotate disks 20, 38, as desired. Such movement can be generated using various different conventional trigger mechanisms which would be connected at a proximal end to cables 50.

It should also be appreciated that while cables 50 are shown as the drive member for disks 20, 38 in accordance with the present invention, other mechanisms for rotating these disks could likewise be used and would be well within the broad scope of the present invention.

Figure 8:
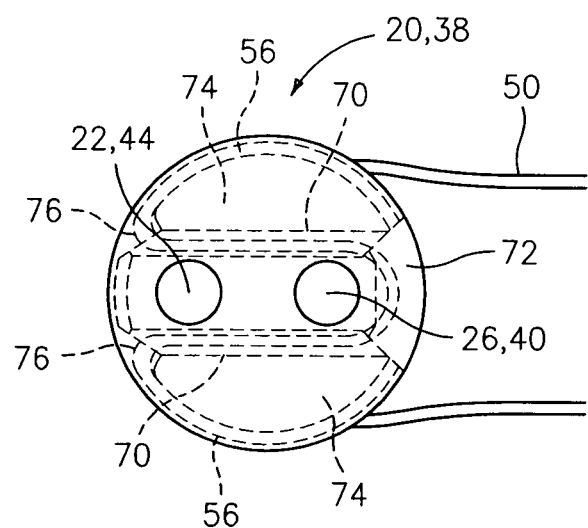
FIGS. 8 and 9 further illustrates the rotatable disk element of the present invention.
Figure 9:
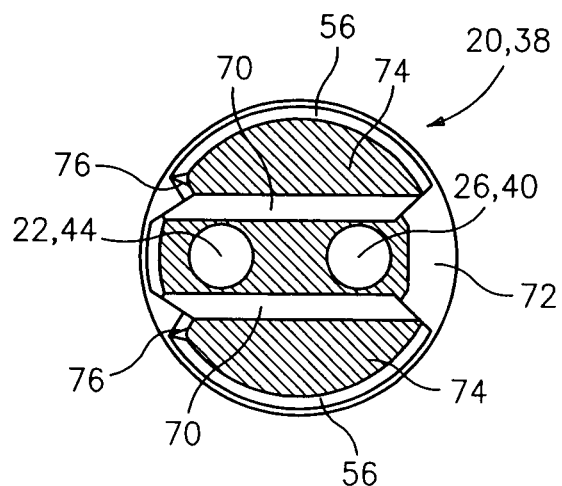

FIGS. 8 and 9 further illustrate disks 20, 38 and a preferred structure for securing cables 50 relative to disks 20, 38. As shown, disks 20, 38 advantageously are provided with two cable passages 70, preferably passing laterally through the disk. FIGS. 8 and 9 show passages 70 spaced from a center of the disk and substantially parallel. Other configurations of passages 70, and one or more than two passages 70 also fall well within the broad scope of the invention. Disks 20, 38 preferably have an inset central portion 72 at one end, between passages 70.

FIG. 8 shows an advantageous positioning of cable 50 according to the invention which cable 50 passes through the peripheral groove 56 on one side into one passage 70, around inset central portion 72, back through the other passage 70, and around the peripheral groove 56 on the other side. In this way, cable 50 is held fast in position relative to disk 20, 38 so that back and forth tensioning of cable 50 rotates the disk as desired.

It should be appreciated that while disks 20, 38 are shown in this embodiment as using passages 70 to secure cable 50, other structures could be used to secure cable 50 and would be well within the broad scope of the present invention.

Still referring to FIGS. 8 and 9, passages 70 and peripheral grooves 56 define there between two circle-segment shaped sections 74 of the disks. At an end of sections 74 facing away from central portion 72, rounded corners 76 can advantageously be provided to smoothly receive cable 50 positioned as shown. In this configuration, it should also be appreciated that inset central portion 72 allows cable 50 to pass through this portion of disks 20, 38 without extending beyond the peripheral edge of the disk, where it might interfere with proper rotation.

It should readily be appreciated that the embodiment of the present invention as illustrated in FIGS. 1-5 above can advantageously be utilized to close jaws of a clamping device while avoiding problems and issues which arise during closing of conventional devices. These problems occur due to "alligator" closing of the jaws, wherein the distal ends of the jaws are spread during the closing procedure.

In the present invention, the embodiment of FIG. 1 can be used to substantially avoid any alligator closing, while the embodiment of FIG. 3 can be used to provide complete control over the orientation of jaws 14, 16 during closing, while the embodiment of FIG. 5 can be used to provide substantial simultaneous operation of the closing mechanism and member for applying a separating force which leads to substantially constant jaw orientation, preferably substantially parallel closing of jaws 14, 16, as desired.

One particular type of surgical instrument with which the closing mechanism can be used is a clamping and stapling mechanism, wherein the jaws 14, 16 also include a plurality of staple-forming mechanisms which are applied to tissue after they are grasped with the jaws. Of course, any type of clamping or other closing mechanism would be well suited for use with the closing mechanism in accordance with the present invention, particularly when "alligator" closing is an issue.

It is to be understood that the invention is not limited to the illustrations described and shown herein, which are deemed to be merely illustrative of the best modes of carrying out the invention, and which are susceptible to modification of form, size, arrangement of parts and details of operation. The invention rather is intended to encompass all such modifications which are within its spirit and scope as defined by the claims.

What is claimed is:

1. A closing assembly for a clamping device having first and second jaw members, comprising:
    a closing mechanism connected between the first and second jaw members, the jaws extending distally from the closing mechanism, wherein the closing member comprises a rotatable member and a drive member for rotating the rotatable member, wherein the drive member comprises a flexible member passing around the rotatable member for pulley-like rotation of the rotatable member responsive to movement of the flexible member; and
    means for applying a separating force to the first and second jaw members proximally of the closing mechanism, whereby the first and second jaw members can be maintained substantially parallel during closing, wherein the rotatable member is rotatably mounted relative to one jaw of the first and second jaw members, and wherein the closing mechanism further comprises a link member movably connected between the other jaw of the first and second jaw members and the rotatable member, whereby rotation of the rotatable member moves the first and second jaw members between an open and a closed position, wherein the rotatable member comprises a disk, and wherein the disk is mounted to the one jaw at a non-centric point relative to the disk, and wherein the link member is also mounted to the disk at another non-centric point relative to the disk.

2. The assembly of claim 1, wherein the drive member rotates the disk relative to the first and second jaw members.

3. The assembly of claim 2, wherein the flexible member passes around the disk for pulley-like rotation of the disk responsive to movement of the flexible member.

4. The assembly of claim 1, wherein the means for applying a separating force comprises a spring member positioned between the first and second jaw member and exerting the separating force against the first and second jaw members.

5. The assembly of claim 4, wherein the spring member is a coiled spring.

6. The assembly of claim 4, wherein the spring member is a leaf spring.

7. The assembly of claim 1, wherein the means for applying a separating force comprises a proximal rotatable member rotatably mounted relative to one jaw of the first and second jaw members, and a link member movably connected between the other jaw of the first and second jaw members and the rotatable member, whereby rotation of the rotatable member applies and removes the separating force.

8. The assembly of claim 7, further comprising a link member rotatably connected to the rotatable member and the proximal rotatable member whereby rotation of one member of the rotatable member and the proximal rotatable member rotates the other member of the rotatable member and the proximal rotatable member.

9. The assembly of claim 8, wherein the drive member also rotates the proximal rotatable member.

10. The assembly of claim 1, wherein the first and second jaw members define a surgical clamp.

11. The assembly of claim 1, wherein the disk has at least one cable passage.

12. The assembly of claim 11, wherein the disk has two substantially lateral cable passages.

13. The assembly of claim 12, further comprising a cable passing through the cable passages.

14. The assembly of claim 13, further comprising an inset central portion defined between the cable passages, and wherein the cable extends from one passage along the inset central portion to the other passage.

15. A closing assembly for a clamping device having first and second jaw members, comprising:
   a closing mechanism connected between the first and second jaw members, the jaws extending distally from the closing mechanism, wherein the closing member comprises a rotatable member and a drive member for rotating the rotatable member, wherein the drive member comprises a flexible member passing around the rotatable member for pulley-like rotation of the rotatable member responsive to movement of the flexible member; and
   means for applying a separating force to the first and second jaw members proximally of the closing mechanism, whereby the first and second jaw members can be maintained substantially parallel during closing, wherein the rotatable member is rotatably mounted relative to one jaw of the first and second jaw members, and wherein the closing mechanism further comprises a link member movably connected between the other jaw of the first and second jaw members and the rotatable member, whereby rotation of the rotatable member moves the first and second jaw members between an open and a closed position, wherein the link member comprises an elongate member pivotably connected at a first point to the rotatable member and pivotably connected at a second point to the other jaw, wherein the first point and the second point are spaced along a length of the elongate member.

* * * * *